United States Patent [19]

Lopapa et al.

[11] 4,393,040
[45] Jul. 12, 1983

[54] IN-VITRO DIAGNOSTIC METHOD FOR DETECTION OF ACETYLSALICYLIC ACID INGESTION

[75] Inventors: Alberto F. Lopapa; Theodore D. Hall, both of Los Angeles, Calif.

[73] Assignee: Lopapa Institute, Inc., Los Angeles, Calif.

[21] Appl. No.: 246,993

[22] Filed: Mar. 24, 1981

[51] Int. Cl.$^3$ .................. G01N 33/56; G01N 33/58; G01N 33/60

[52] U.S. Cl. .................................. 424/1; 436/547; 436/127

[58] Field of Search ............... 424/1, 12; 23/230 B

[56] References Cited

U.S. PATENT DOCUMENTS

| | | | |
|---|---|---|---|
| Re. 29,995 | 4/1979 | Borstein et al. | 424/1 |
| 3,799,740 | 3/1974 | Mincey | 23/230 B |
| 3,867,366 | 2/1975 | Rubenstein et al. | 260/121 |
| 3,938,953 | 2/1976 | Paschalis et al. | 23/230 B |
| 3,940,475 | 2/1976 | Gross | 424/1 |
| 3,949,064 | 4/1976 | Bornstein et al. | 424/1 |
| 3,972,991 | 8/1976 | Caston et al. | 424/1.5 |
| 4,036,823 | 7/1977 | Soares | 260/112 R |
| 4,043,759 | 8/1977 | Charm et al. | 23/230 B |
| 4,053,459 | 10/1977 | Christenson | 260/112 B |
| 4,064,227 | 12/1977 | Brown et al. | 424/1 |
| 4,119,709 | 10/1978 | Holub | 424/1 |
| 4,151,268 | 4/1979 | Spector | 424/1 |
| 4,189,463 | 2/1980 | Dixon | 424/1 |
| 4,196,185 | 4/1980 | Focella et al. | 424/1 |
| 4,197,286 | 4/1980 | Rao | 424/1 |
| 4,197,288 | 4/1980 | Snyder | 424/1 |
| 4,218,436 | 8/1980 | Fitzpatrick | 424/85 |
| 4,220,598 | 9/1980 | Hixson, Jr. et al. | 260/397.1 |
| 4,231,923 | 11/1980 | Miller et al. | 260/112.5 R |
| 4,235,864 | 11/1980 | Kaul et al. | 424/1 |
| 4,235,866 | 11/1980 | Thoma | 424/1 |

Primary Examiner—Christine M. Nucker
Attorney, Agent, or Firm—Frank Frisenda, Jr.

[57] ABSTRACT

An in-vitro diagnostic method is provided for detecting acetylsalicylic acid ingestion by a patient by utilizing radioimmunoassay procedure. The method comprises the steps of: derivatizing acetylsalicylic acid with a protein moiety being effected in a molar ratio of about one mole of protein to at least thirty moles of acetylsalicylic acid; coupling the acetylsalicylic acid derivatized protein with a water insoluble solid matrix by binding with a selected chemical agent; obtaining a sample of patient serum; freeze drying the serum including any antibodies specific to acetylsalicylic acid to concentrate the serum to a solid phase; diluting the freeze dried serum to from about 100 to about 1,000 times its original concentration; incubating the solid matrix coupled with the acetylsalicylic acid derivatized protein with the concentrated serum for a sufficient period of time to allow any antibodies specific to acetylsalicylic acid to attach to the solid matrix coupled with the acetylsalicylic acid derivatized protein, the incubation occurring for at least 24 hours at a temperature range of from about 4° C. to about 42° C.; thereafter, incubating the solid phase bound with specific antibodies present with radioactively labelled antibodies specific to acetylsalicylic acid derivatized protein obtained from a test animal for a sufficient period of time to allow binding between the labelled antibodies and the matrix; separating the mixture into distinct liquid and solid phases; and measuring the radiation emitted from at least one of the separated phases.

8 Claims, No Drawings

IN-VITRO DIAGNOSTIC METHOD FOR DETECTION OF ACETYLSALICYLIC ACID INGESTION

BACKGROUND OF THE INVENTION

This invention relates to in-vitro diagnostic method by radioimmunoassay for the detection of acetylsalicylic acid ingestion by a patient. In particular, the unique method is designed to detect antibodies elicited in the patient's serum responsive to salicylate ingestion.

Acetylsalicylic acid, commonly known as aspirin, is perhaps the most prevalent drug used by the general population to alleviate symptoms of a wide variety of illnesses. However, in recent years, it has been recognized by medical practitioners that there exists a possibility of long-term toxic effects from ingestion of the drug. For example, analgesic nephropathy is one such deleterious effect reported by Spuhler, O. and Zollinger, H. in Helv. Med. Acta, 1950, 17, 564.

Moreover, adverse effects of salicylate ingestion, notably, changes in epithelial-cell excretion rate, tubular handling of electrolyte, acidification, and enzyme excretion have also been studied.

Kimberly and Plotz, in P.H. New England Journal of Medicine 1977, 296, 418, hypothesized that the cause of functional abnormalities from salicylate ingestion is the suppression of prostaglandin synthetase with consequent fall-off in renal profusion.

Remuzzi, G. et al. in "The Lancet", Aug. 13, 1977 at page 359 et seq. have recognized that aspirin should be withheld from patients with chronic renal failure, since it may cause a further decline in renal function and could carry an increased risk of gastrointestinal haemorrhage.

Collins, E. and Turner, G. in "The Lancet", Oct. 9, 1976 at page 797 et seq. report that very few daily takers of aspirin disclosed this information to their physicians during antenatal visits, and many denied taking aspirin—containing powders at the beginning of a postnatal interview until told that they had had salicylate in their urine at every antenatal visit. The purpose of such questioning was to confirm the deleterious effects of apsirin which occur mainly during the last trimester of pregnancy. One such effect was a relatively high stillbirth rate found in the study which was speculated to be caused by salicylate on platelet function.

The techniques of solid-phase RIA of antigens or antibodies are generally known in the art. However, they have not been applied to a system for detecting ASA ingestion. U.S. Pat. No. Re 29,955 to Bornstein et al and U.S. Pat. No. 3,790,663 to Garrison et al., indicate that solid-phase RIA was introduced to the art by Catt and co-workers. The Catt technique involves the bonding of antibodies to a polymeric solid-phase. Accordingly, the bonded antiserum is utilized to selectively bind antigen for which the antiserum is specific. When radioactively labelled antigen is added to the sample being assayed, such as blood or serum, the labelled and unlabelled antigen compete for binding by the antiserum. The more unlabelled antigen competing for the aniserum binding sites the less labelled antigen will be found. Thus, by incubating the coated solid-phase with a specimen to which radioactive labelled antigen has been added and then counting the radiation content of the solid-phase, the antigen concentration of the specimen can be determined. Specific techniques for solid-phase polymers in the RIA field have been reported in Biochem. J. 100: 31C (1966), Science, 158: 1570 (1967) and J. Lab & Clin. Med., 70: 820 (1967) as well as other reported journal articles and patents.

While RIA as applied to general diagnostic methods has been known, the procedure for the assay of antibodies elicited from acetylsalicylic acid ingestion in accordance with the present invention has not. On possible reason for the apparent lack of application is that much of the acetylsalicylic acid ingested is destroyed in the patient's digestive tract with a consequent minute quantity of antibodies produced.

Accordingly, those skilled in the art, have recognized a significant need for a sensitive in-vitro diagnostic method for detecting such ingestion, particularly when the patient is unwilling or unable to convey this critical information to a treating physician.

The present invention fulfills these needs.

SUMMARY OF THE INVENTION

This invention provides an in-vitro diagnostic method for detection of acetylsalicylic acid ingestion by a patient by utilizing radioimmunoassay procedure.

In accordance with one embodiment of the present invention, the method comprises the steps of: derivatizing acetylsalicylic acid with a protein moiety being effected in a molar ratio of about 1 mole of protein to at least 30 moles of acetylsalicylic acid; coupling the acetylsalicylic acid derivatized protein to a water insoluble solid matrix by binding with a suitable coupling agent; obtaining a sample of patient's serum, the patient having been suspected of acetylsalicylic acid ingestion; freeze drying the patient serum including any antibodies specific to acetylsalicylic acid to concentrate the serum to a solid phase; diluting the freeze dried serum from its solid phase to a concentrated solution being of from about 100 to about 1,000 times the serum's original concentration; incubating the solid matrix coupled with the acetylsalicylic acid derivatized protein with the concentrated serum for a sufficient period of time to allow any antibodies specific to acetylsalicylic acid derivatized protein, the incubation occurring for at least 24 hours at a temperature range of from about 4° C. to about 42° C.; thereafter, incubating the solid matrix bound with specific antibodies present with radioactively labelled antibodies specific to acetylsalicylic acid derivatized protein obtained from a test animal for a sufficient period of time to allow binding between the labelled antibodies and the matrix; separating the mixture into distinct liquid and solid phases; and measuring the radiation emitted from at least one of the separated phases.

In a presently preferred embodiment, the radioactively labelled antibodies specific to acetylsalicylic acid derivatized protein is produced by immunizing the test animal, by repeated sub-cutaneous injections of acetylsalicylic acid derivatized protein mixed with suitable adjuvant, for instance, Freund's complete adjuvant mineral oil suspension. Labelling of the antibody recovered from the test animal can be effected with radioactive isotopes, such as $I^{125}$, fluorescent groups, luminescence, enzymes or other conventionally used tagging agents.

Also preferred is the coupling of the acetylsalicylic acid derivatized protein to the solid matrix by binding with suitable coupling agent having reactive group such as amino groups, hydroxyl groups, nitro groups, halo groups, amido groups, carboxylic groups and mixtures thereof.

Other features and advantages of the present invention will become apparent from the following detailed descriptions and the claims appended thereto.

DESCRIPTION OF THE PREFERRED EMBODIMENTS

Initially, it should be noted, that as used in this specification, the term acetylsalicylic acid connotes a composition of the formula: $C_9H_8O_4$ having a molecular weight of about 180.15. More particularly, the composition is defined by the formula $CH_3CO.O.C_6COOH$, carbon being present in an amount of about 60%, hydrogen being present in an amount of about 4.48% and oxygen being present in an amount of about 35.53%. The salicylic acid equivalent is about 76.67%.

The drug is commonly prepared by acetylation of salicylic acid with acetic anhydride, using a small amount of sulphuric acid as catalyst, for instance prepared in accordance with the procedure described in U.S. Pat. No. 2,731,492 issued to Kamlet and U.S. Pat. No. 2,890,240 issued in 1959 and assigned to Monsanto Limited. These patent disclosures are herein incorporated by this reference.

The most common medicinal uses of acetylsalicylic acid are as an analgesic, antipyretic and antipyretic and antirheumatic. Average doses of the drug, for instance, in an amount of from about 0.3 to about 1 gram, but more likely from relatively large doses taken by a patient may cause tinnitus, nausea, vomiting, diarrhea and gastrointestinal bleeding.

In addition, there may be auditory impairment, vertigo, headache, hyperpnea, respiratory failure and even death. It has been noted, that prolonged use of average or large doses may produce hypoprothrombinemia and hemorrhage.

All of the foregoing deleterious toxic effects in addition to those recently noted (as summarized in the background of invention heretofore described) make detection of acetylsalicylic acid ingestion an important diagnostic tool for treating physicians of patients who are unwilling or unable to convey to the physician necessary information regarding previous ingestion of the drug.

Accordingly, there has been recognized by those skilled in the art, a significant need for an effective means for detection of acetylsalicylic acid ingestion by a patient, in order for a treating physician to prescribe additional medication or to correct adverse effects from toxicity of the drug.

The present invention provides an in-vitro diagnostic method for detecting acetylsalicylic acid ingestion by a patient by utilizing radioimmunoassay procedure, which has heretofore been unknown. In more detail, the method in accordance with the present invention comprises the steps of: derivatizing acetylsalicylic acid with a protein moiety being effected in a molar ratio of about 1 mole of protein to at least 30 moles of acetylsalicylic acid; coupling the acetylsalicylic acid derivatized protein with a water insoluble solid matrix by binding with a selected coupling agent; obtaining a sample of patient serum; freeze drying the serum including any antibodies specific to acetylsalicylic acid to concentrate the serum to a solid phase; diluting the freeze dried serum to from about 100 to about 1,000 times its original concentration; incubating the solid matrix coupled with acetylsalicylic acid derivatized protein with the concentrated serum for a sufficient period of time to allow any antibodies specific to acetylsalicylic acid to attach to the solid matrix coupled with the acetylsalicylic derivatized protein, the incubation occurring for at least 24 hours at a temperature range of from about 4° C. to about 42° C.; thereafter, incubating the solid phase bound with specific antibodies present with radioactively labelled antibodies specific to acetylsalicylic acid derivatized protein obtained from a test animal for a sufficient period of time to allow binding between the labelled antibodies and the matrix; separating the mixture into distinct liquid and solid phases; and measuring the radiation from at least one of the separated phases.

The derivatization of acetylsalicylic acid with protein must be carried out in a manner which will sustain the active groups of the drug to subsequently attach with the antibodies present in the patient's serum and labelled antibodies for the radioimmunoassay procedure. Thus, a molar ratio of one mole of protein moiety to at least 30 moles of acetylsalicylic acid must be maintained during the derivatization procedure. In this respect, the molar ratio of acetylsalicylic acid may preferably range from about 30 moles to about 45 moles of the drug to every mole of protein moiety.

The protein moiety must be foreign to the animal species being immunized and immunogenic in character and preferably have a molecular weight of greater than about 6,000. Suitable protein carriers useful in the practice of this invention includes human serum albumin, human immunoglobins, bovine serum albumin, bovine immunoglobulins, keyhole limpet, limulus hemocyanin and mixtures thereof.

The derivatization of acetylsalicylic acid is effected by suitable coupling agents including carbodiimide, isoxazolium salt or the like capable of activating carboxyl groups to form a peptide bond (CO—NH).

Further disclosure regarding the derivatization procedure can be had by reference to "Structural Concepts In Immunology And Immunochemistry" by Elvin Kabat at pages 9 et seq, which is hereby incorporated by this reference. Additionally, Albertson, N. F., In Cope, A. C. edition, Organic Reaction 12, John Wiley & Sons Publisher (1962) at page 159 et seq, provides a more detailed disclosure of the Schiff's base reaction for derivatization which is hereby incorporated by this reference.

The acetylsalicylic acid derivatized with protein is then coupled to a water insoluble solid matrix by suitable coupling agent. The matrix may be constructed in the form of disc, tube, particles, beads and the like, for example, composed of materials such as polystyrene, polyethylene, polypropylene, nitrocellulose, acrylomide, glass or suitable co-polymers such as acrylonitrile with styrene. Accordingly, the matrix should be such that the acetylsalicylic acid derivatized protein will readily bond or attach to the matrix. Preferably, the coupling agent selected for binding have reactive groups selected from the group consisting of amino groups, hydroxyl groups, nitro groups, halo groups, amido groups, carboxylic groups and mixtures thereof. Further disclosure in this regard may be had by reference to "A Solid Phase Disc RIA For Human Growth Hormone", Catt et al J. Lab. & Clin. Med., (November 1967) at page 820 et seq. and "Use of Antibody Bound To Modified Cellulose As An Immunospecific Adsorbent Of Antigens", A. T. Jagendorf et al, published in Biochem. Biophys. Acta., 78 (1963) 516–528 incorporated herein.

The matrix is contacted with the acetylsalicylic acid derivatized protein in a concentration effective to couple the drug-protein complex to the matrix by reacting with the selected coupling agent. In this respect, a suitable buffer may be utilized if dilution of the drug-protein is required. Typical buffers for this purpose include solutions of $H_3BO_3$ and NaOH, conventional carbonate and bicarbonate solutions, mixed with water. The pH of the coupling component should be adjusted to a value of between about 6 and 11 and preferably between about pH 9 and 9.8.

After the drug-protein and coupling agent has been allowed to remain in contact with the solid matrix for a sufficient period of time to allow coupling, the matrix is removed and washed in a conventional manner. Further information in this regard may be had by reference to "Rapid Micro-Radioimmunoassay For The Measurement Of AntiViral Antibodies" authored by Rosenthal et al., the Journal of Immunology, Volume 109, No. 1, pages 171-173, July 1972 which is hereby incorporated by this reference. Additionally, reference may be had to "Sandwich Solid-Phase Radioimmunoassay For the Quantitative Determination of Human Immunoglobulins" by Salmon et al., published in the Journal of Immunology, Volume 3, No. 1, pages 129-137, July 1969, which is further incorporated by this reference.

The sample of patient's serum, the patient having suspected of acetylsalicylic acid ingestion, is lyophilized to a solid-phase by standard technique. The freeze dried serum may thereafter be dissolved in water to give a concentration of from about 100 to about 1,000 times the original concentration of the serum. The matrix coupled with the acetylsalicylic acid derivatized protein is next incubated with the concentrated serum containing antibodies specific to the derivatized coating for from about 24 hours to about 100 hours and preferably for at least about 72 hours at a temperature range of from about 4° C. to about 42° C. to allow sufficient incubation for maximum attachment of the antibodies with the coated matrix. This step is particularly critical in that only small amounts of antibody are originally present in a patient's serum who has ingested acetylsalicylic acid.

A suitable test animal such as a sheep, rabbit, goat or the like, is immunized by repeated sub-cutaneous injections of the aspirin derivatized protein mixed with suitable adjuvant, for instance, Freund's mineral oil suspension in relatively concentrated form. For instance, intraveneous injection may be performed twice weekly for a period of about 5 weeks. The total dose of acetylsalicylic acid derivatized protein administered will be such as to produce the desired concentration of antibodies specific thereto. Blood from the test animal may thereafter be drawn by venipuncture with cardiac puncture about two weeks after the last injection. Typically, for a test animal such as a New Zealand white rabbit weighing about 5 kg, a total dose of between about 300 milligrams to about 800 milligrams of derivatized drug is administered, diluted with no more than about a 1% aqueous solution in normal saline. The serum including specific antibodies is withdrawn from the test animal, separated by centrifugation, and is passed through a conventional solid matrix to isolate the specific antibodies.

The specific antibodies from the test animal's serum is labelled with a radioactive isotope of iodine, such as $I^{125}$ in accordance with known technique. In this regard, reference may be had to the following article entitled "The Preparation of $I^{131}$ Labelled Human Growth Hormone Of High Specific Radioactivity" authored by Greenwood et al., in Biochem. J., Volume 89, 1963, pages 114 et seq. which is hereby incorporated by this reference. Of course, the technique of fluorescence enhancement using a high natural fluorescence emission spectre may also be utilized in accordance with known procedures.

The radioimmunoassay is conducted by providing an amount of labelled antibodies specific to the acetylsalicylic acid derivatized protein into a receptacle and thereafter incubating the matrix coated with the concentrated patient's serum for a sufficient period of time to allow reaction therebetween. Typically, the incubation will take place at room temperature for at least 3 hours and thereafter removing the matrix from the receptacle and washing the matrix in a conventional manner.

Thereafter, the radiation emitted from either the solid matrix or the liquid phase remaining after separation is determined by gamma counting.

Subsequent to measuring, the radiation emitted from either of the phases is measured against known negative controls. If the gamma counting indicates that radiation emitted from the liquid phase is maximal, compared with the known negative, it can be deduced that the patient serum being tested indicates that there has been no acetylsalicylic acid ingested. Likewise, if the solid matrix has a recorded count above the known negative control, then it can be deduced that the patient had ingested acetylsalicylic acid. The establishment of standard curves for the sample to be assayed may be prepared in accordance with known procedure, as will be readily appreciated by those skilled in the art.

The following illustrative example will serve to further define the principles and procedures of the present inventive methods.

EXAMPLE 1.

The derivatization of acetylsalicylic acid is effected with carbodiimide as coupling agent and BSA as the protein moiety selected. The derivatization is performed at room temperature, about 75° F., for the initial combination of acetylsalicylic acid with carbodiimide and completed in a second phase by stirring the solution with BSA at a temperature of about 4° C. for about 12 hours and a pH of about 5.5. The derivatization procedure is defined by the following reactions:

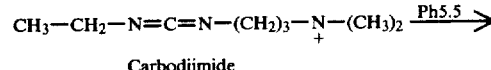
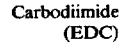
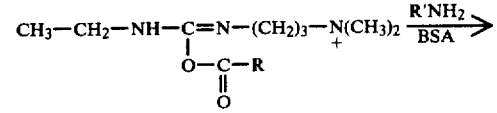
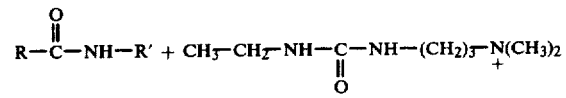

In more detail, approximately 20 milligrams of acetylsalicylic acid dissolved in a 3% by volume water is dissolved by constant stirring and the solution is brought to a pH of about 5.5 with suitable buffers. The coupling agent, carbodiimide and selected protein, BSA, is added to the acetylsalicylic solution in dropwise fashion maintaining the pH at approximately constant level. The resultant solution is then transferred to a cold room that is, about 4° C. with constant stirring of the solution for about a 24 hour period. The solution is dialized against changes utilizing a aqueous solution of about 0.15 M NaCl.

The solid matrix selected is polystyrene discs being about ⅜ inch in diameter of a 100th inch film thickness. The discs are coated with the acetylsalicylic acid derivatized protein by gentle agitation at room temperature with the derivatized protein diluted with about 0.05 M bicarbonate buffer at a pH of about 9.6. Contact between the discs and derivatized protein is maintained for about 17 hours. The coated discs are then washed in conventional fashion for about 3 times with saline and stored in BSA diluent at 4° C.

A sample of human serum or plasma is obtained from a patient suspected of having ingested acetylsalicylic acid. The sample is diluted in a 1:2 ratio with a BSA diluent to a final volume of about 3.0 ml. The sample is thereafter lyphilized in accordance with conventional procedure to concentrate the serum to a solid phase. Thereafter, the freeze dried serum is diluted with BSA diluent to 500 times its original concentration.

The solid matrix coupled with the acetylsalicylic acid derivatized protein is then incubated with the concentrated serum for 72 hours at a temperature of 37° C. to allow any antibodies specific to acetylsalicylic acid to attach to the solid matrix coupled with the acetylsalicylic derivatized protein.

Radioiodinated antibodies specific to acetylsalicylic acid are prepared by the method of Hunter and Greenwood (preparation of iodine-$I^{131}$—labelled Human Hormone of High Specific Activity, Nature 194: 495, 1962) utilizing $I^{125}$ supplied by Radiochemical Center, England. The antibody, before tagging, is obtained from rabbits injected with acetylsalicylic derivatized protein defined above and Freund's adjuvant at intervals of twice weekly for a period of 7 weeks. The specific antibodies are obtained by conventional fractionation in conventional fashion (see for instance Fractionation Of Purified Antibodies To The Dinitrophenyl Group With Cross-Reacting Immunoadsorbents, Cheng et al., Journal of Immunology, 97, No. 6, at page 778 et seq.).

The labelled specific antibodies are incubated with the solid matrix coupled with acetylsalicylic acid derivatized protein for a 72 hour period at 37° C. The matrix is then extracted from the mixture by centrifugation and radiation emitted therefrom is measured by a gamma counter and compared against known standards.

EXAMPLE 2.

The procedure of Example 1 is repeated except as to the following derivatization procedure. For purposes of this example, the coupling agent was isoxazolium salt of the keto form of regent K. Human serum albumin was used as the select protein moiety. The coupling procedure is defined by the following formula:

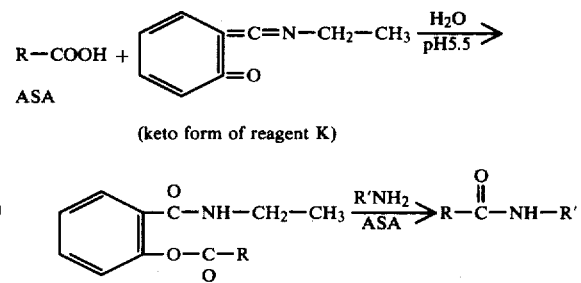

(keto form of reagent K)

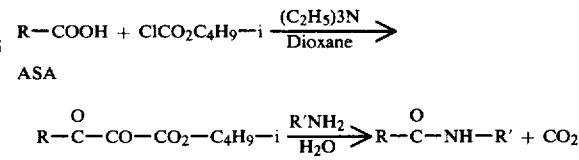

EXAMPLE 3.

The procedure of Example 1 was repeated except that the derivatization of acetylsalicylic acid was conducted as follows: dioxane was utilized as the coupling agent and BSA was utilized as the protein moiety selected. Accordingly, the derivatization procedure is defined by the following formulas:

$$R-COOH + ClCO_2C_4H_9-i \xrightarrow[\text{Dioxane}]{(C_2H_5)3N}$$

ASA $$R-C-CO-CO_2-C_4H_9-i \xrightarrow[H_2O]{R'NH_2} R-\overset{O}{\underset{\|}{C}}-NH-R' + CO_2$$

It will also be apparent that various modifications to the foregoing disclosure can be made by those skilled in the art without departing from the spirit and scope of the invention.

We claim:

1. An in-vitro diagnostic method for detecting acetylsalicylic acid ingestion by a patient by utilizing radioimmunoassay procedure, the method comprising the steps of:
   (a) derivatizing acetylsalicylic acid with a protein moiety, said derivatizing procedure being effected in a molar ratio of about 1 mole of protein to at least 30 moles of acetylsalicylic acid;
   (b) coupling the acetylsalicylic acid derivatized protein obtained from step (a) with a water insoluble solid matrix, said coupling being effected with a coupling agent having a reactive group selected from the group consisting of amino groups, hydroxyl groups, nitro groups, halo groups, amido groups, carboxylic groups and mixtures thereof;
   (c) obtaining a sample of serum from a patient suspected of having ingested acetylsalicylic acid;
   (d) lyophilizing said serum including any antibodies specific to acetylsalicylic acid to concentrate said serum to a solid phase;
   (e) diluting said lyophilized serum to from about 100 to about 1,000 times the serum's original concentration;
   (f) incubating said solid matrix coupled with the acetylsalicylic acid derivatized protein with said concentrated serum for a sufficient period of time to allow any antibodies specific to acetylsalicylic acid to attach to said solid matrix coupled with the acetylsalicylic acid derivatized protein, said incubation occurring for a period of at least 24 hours at a temperature of from about 4° C. to about 42° C.;
   (g) thereafter, incubating said solid matrix bound with specific antibodies present with radioactively labelled antibodies specific to acetylsalicylic acid derivatized protein obtained from a test animal for a sufficient period of time to allow binding between said labelled antibodies and said solid matrix obtained from step (f);

(h) separating the solid matrix from the liquid phase;

(i) and measuring radiation emitted from at least one of the separated phases.

2. The method as defined in claim 1 wherein the step of derivatizing is effected in a molar ratio of about 1 mole of protein to from about 30 to about 45 moles of acetylsalicylic acid.

3. The method as defined in claim 1 wherein said protein moiety has a molecular weight of greater than about 6,000.

4. The method as defined in claim 1 wherein said protein moiety is selected from the group consisting of human serum albumin, human immunoglobulins, bovine serum albumin, bovine immunoglobulins, keyhole limpet, limulus hemocyanin and mixtures thereof.

5. The method as defined in claim 1 wherein said step of incubating said concentrated serum with said coated solid matrix obtained from step (b) occurs for a period of time from about 24 hours to about 100 hours at a temperature range of from 4° C. to about 42° C.

6. The method as defined in claim 1 wherein said radioactively labelled antibodies specific to acetylsalicylic acid derivatized protein is prepared by immunizing said test animal with repeated sub-cutaneous injections of acetylsalicylic acid derivatized protein mixed with adjuvant.

7. The method as defined in claim 6 wherein said adjuvant is Freund's mineral oil suspension.

8. The method as defined in claim 1 wherein said radioactively labelled antibodies specific to acetylsalicylic acid derivatized protein are labelled with radioactive isotopes of iodine.

* * * * *